United States Patent
Wang et al.

(10) Patent No.: US 10,493,583 B2
(45) Date of Patent: Dec. 3, 2019

(54) DETECTION DEVICE, DETECTION METHOD AND COMPENSATION METHOD FOR TOOL WEAR

(71) Applicant: INDUSTRIAL TECHNOLOGY RESEARCH INSTITUTE, Hsinchu (TW)

(72) Inventors: Ming-Jheng Wang, Hualien County (TW); Meng-Chiu Lin, Taichung (TW); Chung-Min Chang, Taichung (TW); Min-Rong Chen, Changhua County (TW); Chien-Yi Lee, Taichung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 50 days.

(21) Appl. No.: 15/854,601

(22) Filed: Dec. 26, 2017

(65) Prior Publication Data

US 2019/0143467 A1   May 16, 2019

(30) Foreign Application Priority Data

Nov. 16, 2017  (TW) .............................. 106139778 A

(51) Int. Cl.
  *B23Q 15/16*   (2006.01)
  *G01N 3/58*   (2006.01)
  (Continued)

(52) U.S. Cl.
  CPC .............. *B23Q 15/16* (2013.01); *G01N 3/58* (2013.01); *G05B 19/404* (2013.01);
  (Continued)

(58) Field of Classification Search
  None
  See application file for complete search history.

(56) References Cited

U.S. PATENT DOCUMENTS

| 4,694,686 A | 9/1987 | Fildes et al. |
| 4,802,095 A | 1/1989 | Jeppsson |

(Continued)

FOREIGN PATENT DOCUMENTS

| CN | 105834835 A | 8/2016 |
| CN | 106475855 A | 3/2017 |

(Continued)

OTHER PUBLICATIONS

TW Office Action in application No. 106139778 dated Sep. 10, 2018.

(Continued)

*Primary Examiner* — Jason Lin
(74) *Attorney, Agent, or Firm* — Maschoff Brennan

(57) ABSTRACT

A detection device, detection method, and compensation method for tool wear, applied to a machine tool including a spindle connected to a tool. A first parameter set including a first cutting depth having a zero cutting depth is set, and the machine tool performs a cutting procedure with the first parameter set to record a first loading rate of the spindle. A second parameter set including a second cutting depth having a non-zero cutting depth is set, and the machine tool performs the cutting procedure with the second parameter set to record a second loading rate of the spindle. A processing device calculates an estimated cutting force according to the loading rates and a machine performance database. A fuzzy logic unit outputs a wear level according to a tool wear database and the estimated cutting force. The machine tool adjusts a cutting locus according to the wear level.

20 Claims, 4 Drawing Sheets

(51) Int. Cl.
*G05B 19/404* (2006.01)
*G05B 19/4065* (2006.01)

(52) U.S. Cl.
CPC .... *G05B 19/4065* (2013.01); *B23Q 2220/006* (2013.01); *B23Q 2717/006* (2013.01); *G05B 2219/35168* (2013.01); *G05B 2219/37228* (2013.01)

(56) References Cited

U.S. PATENT DOCUMENTS

| | | | |
|---|---|---|---|
| 4,831,365 | A | 5/1989 | Thomas et al. |
| 5,407,265 | A | 4/1995 | Hamidieh et al. |
| 5,602,347 | A | 2/1997 | Matsubara et al. |
| 6,732,056 | B2 | 5/2004 | Kluft et al. |
| 2006/0089742 | A1 | 4/2006 | Jalluri et al. |
| 2008/0161959 | A1 | 7/2008 | Jerard et al. |
| 2013/0253670 | A1 | 9/2013 | Chung et al. |
| 2013/0268110 | A1* | 10/2013 | Hamada ............... G05B 19/404 700/192 |
| 2016/0290906 | A1* | 10/2016 | Rancic .................. G01N 3/56 |
| 2017/0315535 | A1* | 11/2017 | Ishii ..................... G05B 19/402 |

FOREIGN PATENT DOCUMENTS

| | | |
|---|---|---|
| EP | 0649704 A1 | 4/1995 |
| JP | 2006-130604 A | 5/2006 |
| TW | I422460 B | 7/2012 |
| TW | I453557 B | 2/2014 |
| TW | M498647 U | 4/2015 |
| TW | M516718 U | 2/2016 |
| TW | 201716179 A | 5/2017 |

OTHER PUBLICATIONS

"A summary of methods applied to tool condition monitoring in drilling" in pp. 997-1010 in "2002 International Journal of Machine Tools & Manufacture" by E.Jantune, Mar. 22, 2002.

"Application of AE and cutting force signals in tool condition monitoring in micro-milling" in pp. 97-102 in "2008 CIRP Journal of Manufacturing Science and Technology" by K. Jemielniak and P.J. Arrazola, Nov. 8, 2008.

"Drill wear monitoring using cutting force signals" in pp. 533-548 in "2004 Mechatronics" by H.M.Ertunc and C. Oysu, Jun. 2004.

"Tool wear predictability estimation in milling based" in pp. 509-521 in "2016 International Journal of Machine Tools & Manufacture" by P.Stavropoulos and A.Papacharalampopoulos and E.Vasiliadis. G.C hryssolouris, Jan. 2016.

"Wavelet analysis of sensor signals for tool condition monitoring" in p. 537-553 in "2009 International Journal of Machine Tools & Manufacture" by Z.Kunpeng and W.Y. San and H.G.Soon, Feb. 12, 2009.

Tool Wear Fuzzy Detection Based on the Machine Tool's Spondle Load, Wang Mingzheng, Jul. 2006.

* cited by examiner

DETECTION DEVICE, DETECTION METHOD AND COMPENSATION METHOD FOR TOOL WEAR

CROSS-REFERENCE TO RELATED APPLICATIONS

This non-provisional application claims priority under 35 U.S.C. § 119(a) on Patent Application No(s). 106139778 filed in Taiwan, R.O.C. on Nov. 16, 2017, the entire contents of which are hereby incorporated by reference.

TECHNICAL FIELD

The disclosure relates to a detection device, detection method, and compensation method for tool wear.

BACKGROUND

The advance of industrial technologies has led to the wide use of computer numerical control machine tools in workpiece production, and the development trend of the next-generation workpiece production is towards unmanned machining and automated production. The higher the degree of automation of a factory, the more the personnel cost in machining process can be saved. However, to ensure the good quality of machined products and the normal operation of production lines, the high-degree automation requires more detection components for detecting the statuses of the production equipment in the manufacturing process as replacing the conventional inspection based on human eyes. The manufacturing of various machine parts is carried out usually by some machining methods, such as milling, drilling and turning. Milling is using a milling machine to hold a metal material on a table and then translate a tool or a cutter in the X axis or the Y axis according to a machining position and spin the tool about the Z axis as the cutter rotation axis relative to such an unfinished workpiece, so that unwanted parts are shaved off from the unfinished workpiece by the upward and downward milling. Considering the enhancement of production capacity, one or more CNC machine instructions may be given to control a cutter to spin for a long time. However, if not all chips are estimated or a wrong machining parameter is used the machining process, the temperature of the tool will increase so that the cutting resistance will increase. In this case, if this abnormal status of the tool is not detected in real time, the lifespan of the machining cutter will reduce or the CNC machine will shut down. Even, when severe wear or a tool fracture occurs on a tool, the product yield rate drops down and thus, the schedule of shipping and the production capacity will be affected.

As aforementioned, the monitoring of cutter status plays a significant role in a machining process. The status of a cutter not only is associated with the cost of the production equipment but also affects the quality of machined products. Both cutter breakage and cutter wear cause the reducing of the product quality. Although some detection methods for directly measuring cutter statuses by laser light, resistances, the optics and air pressures, and some detection method for indirectly estimating cutter statuses by temperatures, vibrations, the engine power or the thermoelectric effect are provided nowadays, these methods requires additional sensors, e.g. laser transceivers, accelerometer, etc. Moreover, sometimes the time for the tool to move away from a respective workpiece may be lengthened in order to satisfy the working conditions of various sensors, and thus, the production efficiency of a machine tool decreases. Further, the installation and maintenance of sensors causes a higher manufacturing cost, and an additional time for repairing or replacing the sensors installed near the tool is also required since they are easily damaged by cut-off chips or cutting fluids. In addition, the monitoring methods of tools usually provide only two statuses indicating the estimated wear level of a respective tool: "Normal! Unnecessary to replace" or "Worn! Necessary to replace." Without the more detailed determination of tool statuses, an accessible tool having slight wear may be replaced ahead of schedule. This also increases the expenditure on the production equipment.

SUMMARY

According to one or more embodiments, the present disclosure provides a detection method for tool wear, applied to a machine tool in which a spindle is connected to a tool. The method includes the following steps. The machine tool is furnished with a first parameter set which includes a first cutting depth having a zero cutting depth (i.e. the first cutting depth is 0). The machine tool and the tool performs a cutting procedure with the first parameter set, and a storage device records a first loading rate of the spindle when the cutting procedure is being executed. After the cutting procedure is performed with the first parameter set, the machine tool is furnished with a second parameter set which includes a second cutting depth having a non-zero cutting depth (i.e. the second cutting depth is not 0). The machine tool and the tool perform the cutting procedure with the second parameter set, and the storage device records a second loading rate of the spindle when the cutting procedure is being executed. The operation device calculates an estimated cutting force according to the first and second loading rates and a machine performance database. A fuzzy logic unit in the operation device outputs a wear level according to the tool wear database and the estimated cutting force.

According to one or more embodiments, the present disclosure provides a compensation method for tool wear, applied to a machine tool in which a spindle is connected to a tool. The method includes the following steps. The machine tool is furnished with a first parameter set which includes a first cutting depth having a zero cutting depth. The machine tool and the tool perform a cutting procedure with the first parameter set, and a storage device records a first loading rate of the spindle when the cutting procedure is being executed. After the cutting procedure is performed with the first parameter set, the machine tool is furnished by a second parameter set which includes a second cutting depth having a non-zero cutting depth. The machine tool and the tool perform the cutting procedure with the second parameter set, and the storage device records a second loading rate of the spindle when the cutting procedure is being executed. The operation device calculates an estimated cutting force according to the first and second loading rates and a machine performance database. A fuzzy logic unit in the operation device outputs a wear level according to the tool wear database and the estimated cutting force. The machine tool adjusts a cutting locus for the tool according to the wear level.

According to one or more embodiments, the present disclosure provides a detection device for tool wear, applied to a machine tool in which a spindle is connected to a tool. The detection device includes a control device, an operation device, and a storage device. The control device performs a cutting procedure respectively with a parameter set and another parameter set, and outputs a loading rate when the cutting procedure is being executed respectively. The parameter sets are different from each other in machining parameter. The operation device is electrically connected to the control device. The operation device is configured to calculate a wear coefficient set according to the loading rates, and calculates an estimated cutting force according to the respective loading rate and a machine performance database. The operation device includes a fuzzy logic unit for outputting a wear level according to the estimated cutting force and the tool wear database. The storage device is electrically connected to the control device and the operation device. The storage device includes the tool wear database, a loading rate database and a machine performance database. The tool wear database is used to store the another parameter set and an actual cutting force corresponding to the another parameter set. The loading rate database is used to store the respective loading rate when the cutting procedure is being executed respectively. The machine performance database is used to store the parameter sets and the wear coefficient set.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

Figure 1:
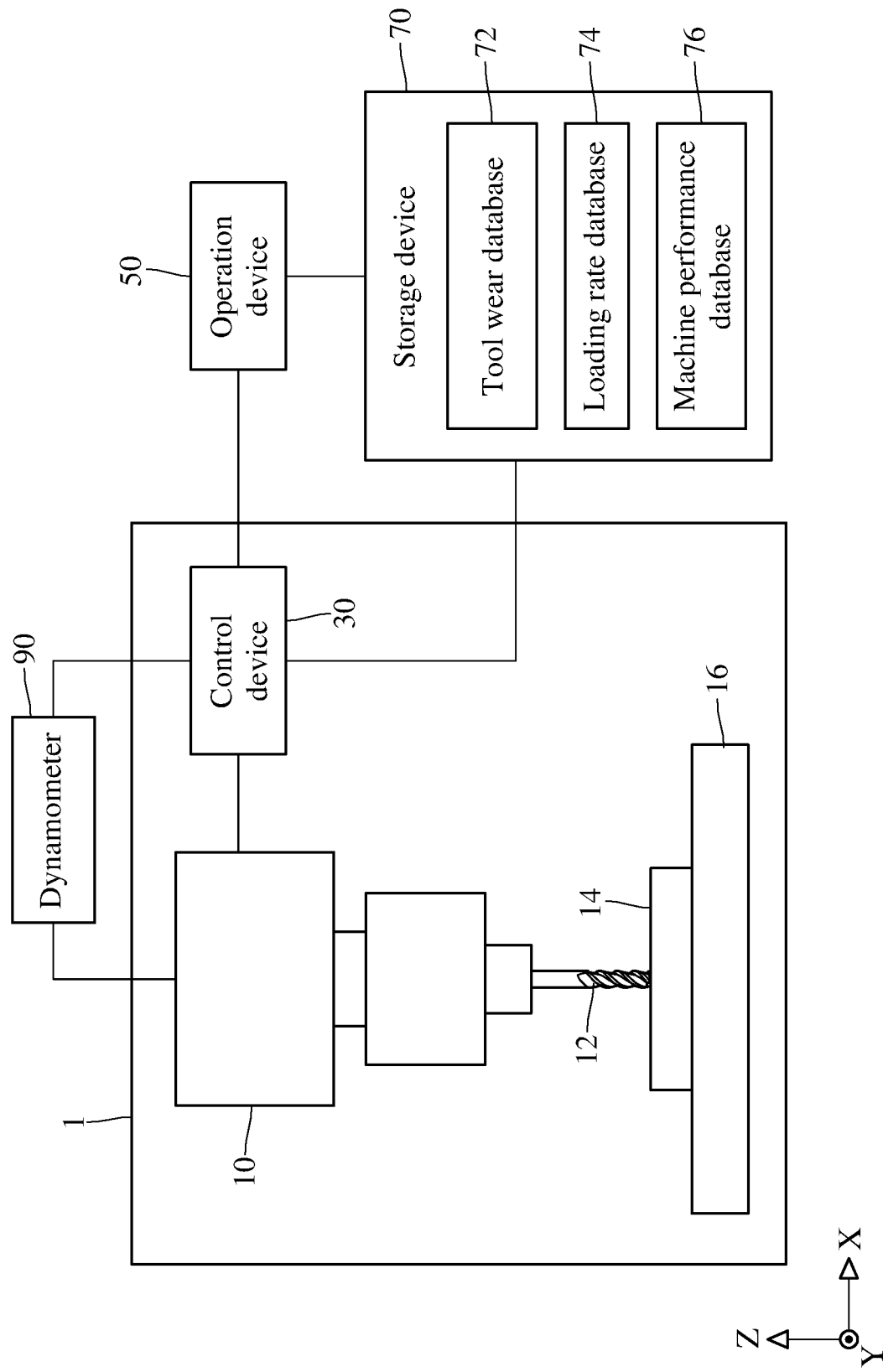
FIG. 1 is a block diagram of a wear detection device for a tool according to an embodiment of the prevent disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Please refer to FIG. 1. The wear detection device for a tool provided in the present disclosure can be applied to a machine tool 1 and a spindle 10 thereof connected to a tool 12. The machine tool 1 includes the spindle 10, a work platform 16 and a control device 30. A workpiece 14 is disposed on the work platform 16. The tool 12 is driven by the spindle 10 to spin. The spindle 10 moves in the X axis or Y axis, so as to decide a cutting position on the workpiece 14 for the tool 12; and the spindle 10 moves in the Z axis, so as to decide a cutting depth in the workpiece 14 for the tool 12.

In an embodiment of the present disclosure, the wear detection device for a tool includes the control device 30 in the machine tool 1, an operation device 50 and a storage device 70. The operation device 50 is electrically connected to the control device 30, and the storage device 70 is electrically connected to the control device 30 and the operation device 50. The storage device 70 includes a tool wear database 72, a loading rate database 74 and a machine performance database 76. The operations of the above devices will be explained later along with the steps in the detection method and compensation method for tool wear provided in the present disclosure.

Figure 2:
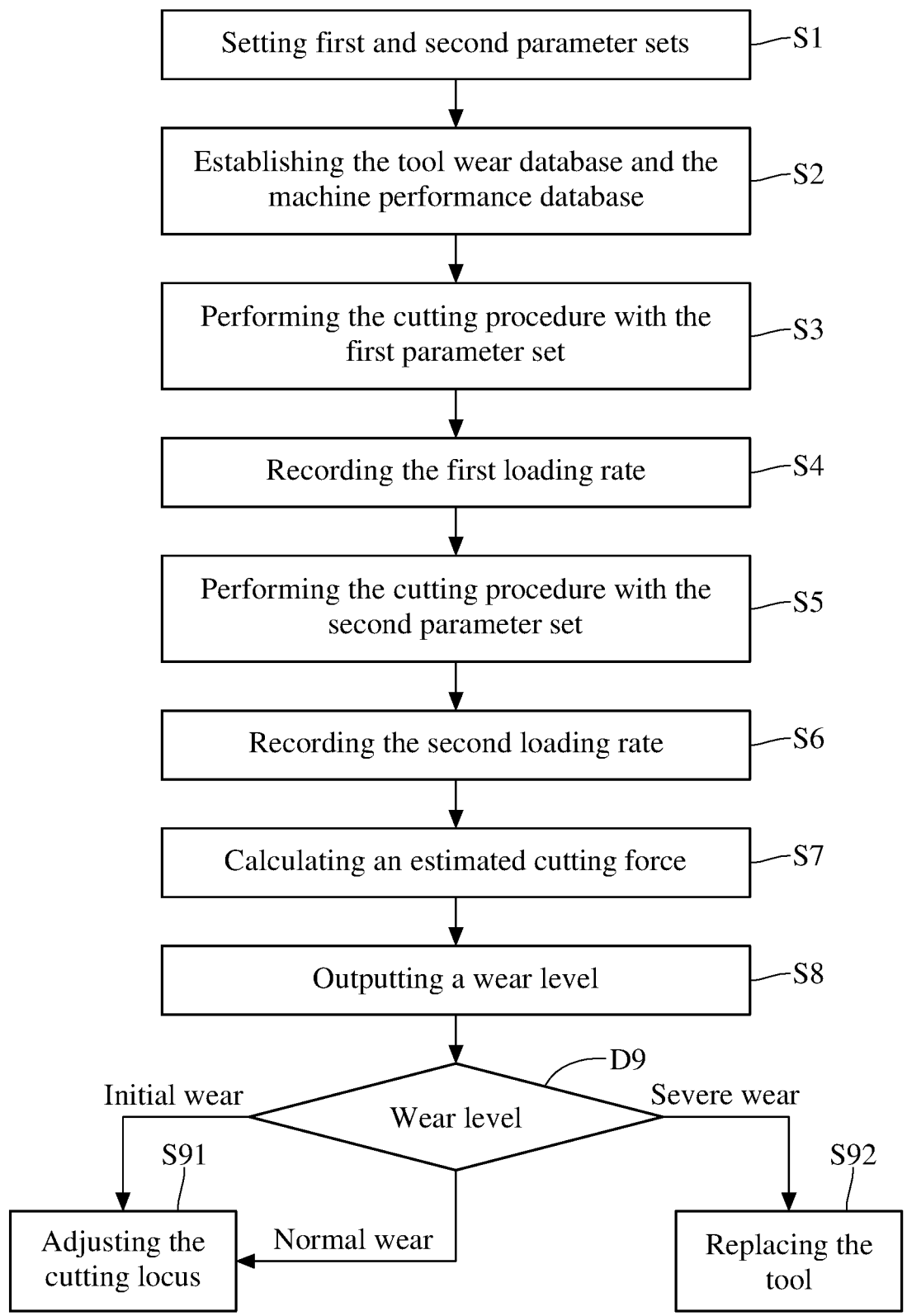
FIG. 2 is a flow chart of a detection method for tool wear according to an embodiment of the prevent disclosure.

Please refer to FIG. 2, which illustrates a detection method and a compensation method for tool wear for a tool according to an embodiment of the present disclosure. Firstly, one or more machining conditions are set. Specifically, as shown in step S1, a first parameter set and a second parameter set are set for the tool 12 by the control device 30. In practice, the control device 30 in the machine tool 1 may include a display and a control board. The display can show machining information, and the control broad allows a user to input one or more machining parameter sets. The machining parameter set in an example includes: rotational speed, feeding rate, cutting depth, cutting width, etc., and the disclosure does not intend to limit the types of parameters in the machining parameter set.

The first parameter set and the second parameter set are two different settings in machining parameter set, wherein the first parameter set is the same as the second parameter set in rotational speed, feeding rate and cutting width, but is different from the second parameter set in cutting depth. In detail, the cutting depth in the first parameter set is 0, which indicates that the tool 12 does not touch the workpiece 14 and is in free running when the machine tool 1 performs a cutting procedure in the first parameter set. The cutting depth in the second parameter set is not 0, which indicates that the tool 12 touches the workpiece 14 and machines the workpiece 14 by the cutting depth when the machine tool 1 performs a cutting procedure by the second parameter set.

As shown in step S2 in FIG. 2, if the tool wear database 72 and the machine performance database 76 have not existed, they should be established before the cutting procedure onto the tool 12, since the operation device 50 needs the information stored in the two databases while calculating the wear level of the tool 12 in the detection method for tool wear. However, if the two databases have existed before the cutting procedure, step S2 can be ignored in the detection method for tool wear and the process directly proceeds to step S3. The tool wear database 72 and the machine performance database 76 are, for example, tables stored in the storage device 70, e.g. a non-volatile storage medium, such as a hard disk drive, a flash memory, or the like.

To establish the above two databases, the wear detection device provided in the present disclosure, as shown in FIG. 1, further includes a dynamometer 90. The dynamometer 90 is electrically connected to the spindle 10 and the control device 30. The dynamometer 90 is used to measure an actual cutting force of the respective tool sample when the cutting procedure is being executed. For example, the dynamometer 90 is a rotary type dynamometer, which is connected to the spindle 10 through piezoelectric crystals, and produces a voltage signal with the spinning of the spindle, and the voltage signal is converted into an actual cutting force or an actual cutting torque by an analog to digital converter.

The existence of the tool wear database 72 makes the wear level of the tool 12 more precise. In this case, the wear level of the tool 12 may be classified into one of three classifications according to the amount of wear of the tool 12 in the unit of mm, such as initial wear (e.g. the amount of wear of about 0.1 mm), normal wear (e.g. the amount of wear of 0.3 mm) and severe wear (e.g. the amount of wear of 0.5 mm), but the disclosure is not limited to the above values and/or the number of classifications of wear level.

To obtain a precise wear level of the tool 12 in real time in the long-term cutting process of the tool 12, it is required to obtain data of the actual cutting forces of tool samples having various wear levels before the machining of workpieces, and thus, the data can be used as a reference for determining the wear level of the tool 12 during the machining of workpieces. In detail, at least one tool sample having initial wear, at least one tool sample having normal wear, and at least one tool sample having severe wear are used. One of the tool samples of three different wear levels is connected to the spindle 10, and then the machine tool 1, according to a second parameter set, performs a cutting procedure, in which, as shown in FIG. 1, the dynamometer 90 measures and obtains an actual cutting force and then stores it in the tool wear database 72. Next, the actual cutting forces of the other two tool samples are respectively collected in the same manner as described above. Therefore, the measurement of actual cutting force is totally performed at least three times in this process, and the results thereof are recorded. An example of the recording manner in a tool wear database 72 is expressed in the following table, in which the rotational speed, the feeding rate and the cutting depth are setting values in the second parameter set. In practice, the design of machining parameter sets depends on the material and type of the workpiece 14. Accordingly, it is required to measure actual cutting forces corresponding to new machining parameter sets by the dynamometer 90 and add the measurement results into the tool wear database 72.

Exemplary Recording Table of Tool Wear Database

| Wear (mm) | Rotational speed (rpm) | Feeding rate (mm/min) | Cutting depth (mm) | Actual cutting force (N) |
|---|---|---|---|---|
| 0.1 | 2500 | 344 | 1 | 76.850 |
| 0.3 | 2500 | 344 | 1 | 80.340 |
| 0.5 | 2500 | 344 | 1 | 94.697 |

The machine performance database 76 is established to provide one or more wear coefficient sets to the operation device 50 for the calculation of the cutting power. The recorded content in the machine performance database 76 will be described with reference to the loading rate of the spindle 10.

Please refer to steps S3-S4 in FIG. 2. The control device 30 controls the machine tool 1 according to the first parameter set to perform a cutting procedure. During the cutting procedure, in addition to showing the loading rate on the display, the control device 30 also stores the loading rate into the loading rate database 74 one time per pulse so that the operation device 50 can use the data in real time. The loading rate outputted by the control device 30 is actually the result of dividing a rated current value by an actual current value. As shown in steps S5-S6 in FIG. 2, after the machine tool 1 performs the cutting procedure according to the first parameter set, the machine tool 1 performs the cutting procedure according to the second parameter set. As the same as steps S3-S4 described above, the control device 30 shows the loading rate on the display and stores the data in the loading rate database 74 when the cutting procedure is being executed, so that the operation device 50 can use the data in real time.

Refer to step S7 in FIG. 2. the loading rates obtained in step S4 and step S6 are subjected to transform several times by the operation device 50, so as to obtain the estimated cutting force of the tool 12. Specifically, the relationship between the loading rate and the power is expressed as follows.

$$P = T \times \omega \qquad \text{(Formula 1)},$$

wherein P denotes a power, T denotes a loading rate, and ω denotes an angular velocity, and the angular velocity can be obtained by converting the rotational speed in the machining parameter set.

Power P is a function of time t. Therefore, in an embodiment of the present disclosure, a free-load power Pu(t) can be obtained by using the formula 1 to convert the loading rate, which is measured when the cutting procedure is performed by the machine tool 1 according to the first parameter set; and a total power Pi(t) can be obtained by using the formula 1 to convert the loading rate, which is measured when the cutting procedure is performed by the machine tool 1 with the second parameter set. The relationship between the total power Pi(t) and the free-load power Pu(t) is expressed as follows:

$$P_i(t) = P_u(t) + P_c(t) + P_a(t) \qquad \text{(Formula 2)},$$

where Pc(t) denotes a cutting power, and Pa(t) denotes an additional power consumption. From the formula 2, it can be known that the total power Pi(t) is a sum of the free-load power Pu(t), the cutting power Pc(t) and the additional power consumption Pa(t). The total power Pi(t) and the free-load power Pu(t) are calculated using the loading rate and the rotational speed by the operation device 50. The additional power consumption Pa(t) is associated with the component wear of the transmission mechanism of the spindle 10, such as a gear, a bearing or a belt. In general, it is difficult to directly and accurately measure the additional power consumption Pa(t), but the additional power consumption Pa(t) and the cutting power Pc(t) have a positive proportion therebetween as follows:

$$P_a(t) = \alpha_1 P_c^2(t) + \alpha_2 P_c(t) \qquad \text{(Formula 3)},$$

Wherein α1 and α2 denote wear coefficient sets.

Then, the formula 3 is substituted into Pa(t) in the formula 2 to obtain an equation as follows:

$$\alpha_1 P_c^2(t) + (1+\alpha_2)P_c(t) + (P_u(t) - P_i(t)) = 0 \qquad \text{(Formula 4)}.$$

To find the two unknown values α1 and α2 of the wear coefficient set, the operation device 50 substitutes a set of free-load powers Pu(t) and a set of total powers Pi(t) obtained above into the formula 4, and when the machine tool 1 measures the actual cutting force by the dynamometer 90, the operation device 50 calculates a cutting power Pc(t) using the actual cutting force by, for example, the following formula.

$$P_c(t) = F_c \times V_c \qquad \text{(Formula 5)}.$$

Wherein Fc denotes a cutting force, and Vc denotes a cutting linear velocity which can be calculated by the rotational speed in the machining parameter set. Furthermore, the control device 30 needs to obtain a second set of total powers Pi2(t) and a second set of cutting powers Pc2(t) by controlling the machine tool 1 to perform the cutting procedure according to another machining parameter set. After the operation device 50 obtains the total powers Pi(t) and Pi2(t) and the cutting powers Pc(t) and Pc2(t) derived through the at least two cutting procedures, the operation device 50 can find the wear coefficient sets α1 and α2 and store the wear coefficient sets and the machining parameter sets into the machine performance database 76. In practice, to reduce errors caused by human or random factors, step S2 is executed to perform the cutting procedure more than two times based on a variety of machining parameter sets and then calculate a wear coefficient set by the method of least squares. The machine performance database 76 records wear coefficient sets and machining parameter sets corresponding to the wear coefficient sets. After the machine performance database 76 is established, the operation device 50 acquires the free-load power Pu(t) recorded in step S4 and the total power Pi(t) recorded in step S6 from the loading rate database 74, and acquires the wear coefficient sets α1 and α2 from the machine performance database 76, and then the operation device 50 substitutes them into the formula 6 to calculate and obtain the cutting power Pc(t) of the tool 12 in this detection task.

$$P_c(t) = \frac{-(1+\alpha_2) + \sqrt{(1+\alpha_2)^2 + 4\alpha_1(P_i(t) - P_u(t))}}{2\alpha_1} \quad \text{(Formula 6)}$$

Next, the operation device 50 converts the cutting power Pc(t) of the tool 12 obtained in this detection task into an estimated cutting force by the formula 5. As aforementioned, the operation device 50, in step S7 shown in FIG. 2, can calculate and obtain an estimated cutting force of the tool 12 under an actual cutting work in this detection task by sequentially using the formula 1 to the formula 6 and using the loading rates issued in the two cutting procedures (the free running and actual cutting work of the tool), and the rotational speed information in the first and second parameter sets. All the wear coefficient sets obtained in the calculation process shall be recorded into the machine performance database 76 for the later measurement.

Refer to step S8 shown in FIG. 2. In an embodiment of the present disclosure, the operation device 50 further includes a fuzzy logic unit. The fuzzy logic unit includes a triangular membership function as follows:

$$\begin{cases} \mu_1(F_c) = \frac{F_2 - F_c}{F_2 - F_1}, & \text{at } F_1 \leq F_c \leq F_2 \\ \mu_1(F_c) = 1, & \text{at } F_c \leq F_1 \\ \mu_1(F_c) = 0, & \text{at neither } F_1 \leq F_c \leq F_2 \text{ nor } F_c \leq F_1 \end{cases}$$

$$\begin{cases} \mu_2(F_c) = \frac{F_2 - F_c}{F_2 - F_1}, & \text{at } F_1 \leq F_c \leq F_2 \\ \mu_2(F_c) = \frac{F_3 - F_c}{F_3 - F_2}, & \text{at } F_2 \leq F_c \leq F_3 \\ \mu_2(F_c) = 0, & \text{at neither } F_1 \leq F_c \leq F_2 \\ & \text{nor } F_2 \leq F_c \leq F_3 \end{cases}$$

and $$\begin{cases} \mu_3(F_c) = \frac{F_c - F_2}{F_3 - F_2}, & \text{at } F_2 \leq F_c \leq F_3 \\ \mu_3(F_c) = 1, & \text{at } F_c \geq F_3 \\ \mu_3(F_c) = 0, & \text{at neither } F_2 \leq F_c \leq F_3 \text{ nor } F_c \geq F_3 \end{cases}$$

Figure 3:
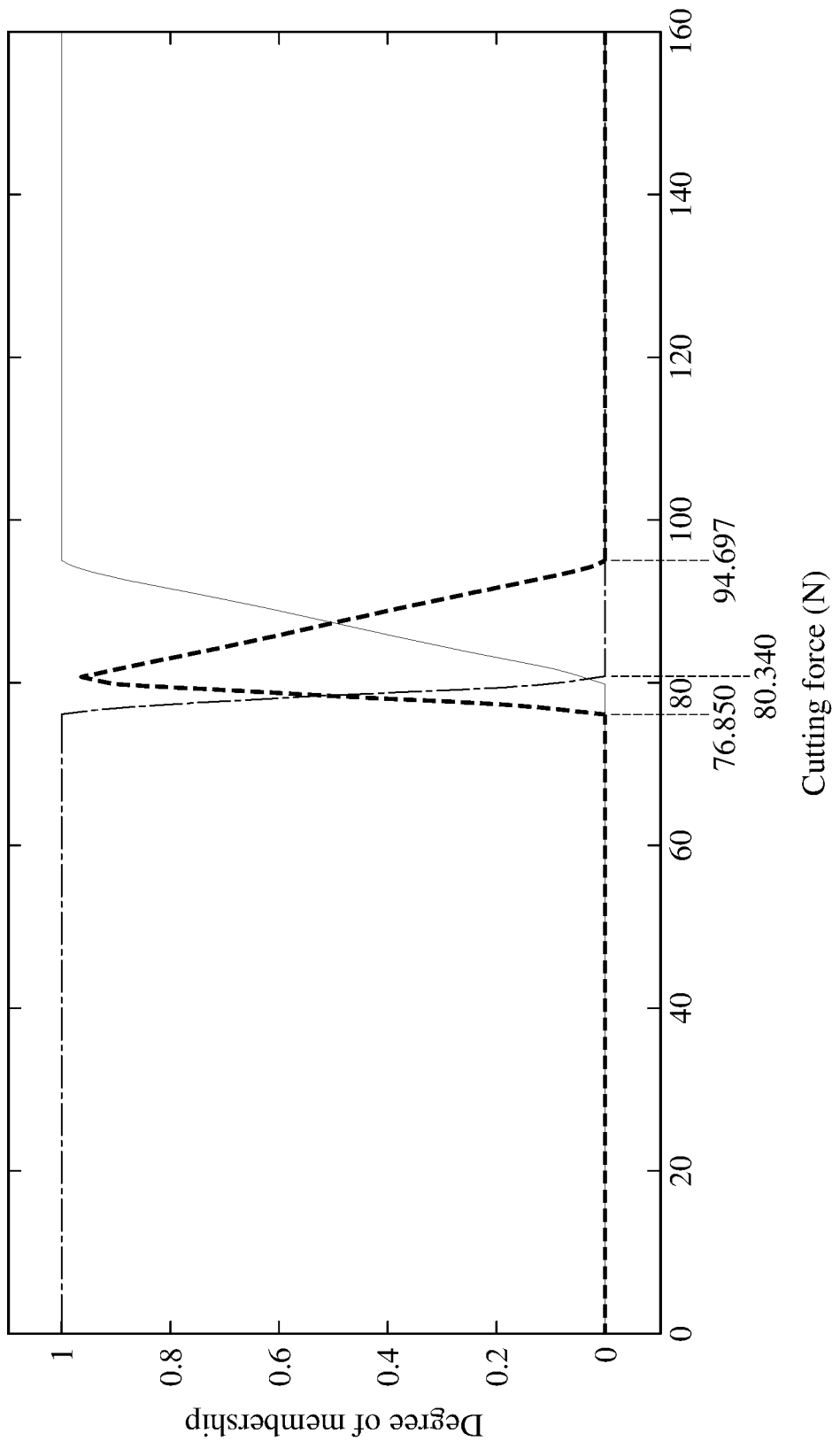
FIG. 3 is a view illustrating a fuzzy set triangular membership function according to an embodiment of the prevent disclosure.

(Formula 7)

Wherein μ1, μ2 and μ3 respectively denote membership functions for initial wear, normal wear and severe wear, and the details thereof will be explained later; Fc denotes the estimated cutting force calculated in step S7; and F1, F2 and F3 respectively denote an initial wear cutting force, a normal wear cutting force and a severe wear cutting force, they are the actual cutting forces measured by the dynamometer 90 during the establishing of the tool wear database 72. FIG. 3 illustrates a triangular membership function according to the formula 7 and three sets of actual cutting forces in the exemplary table in the tool wear database.

The fuzzy logic unit further includes the following five fuzzy set determination rules for determining the wear level:

μ1(Fc)>μ2(Fc) and μ1(Fc)>μ3(Fc): initial wear.

μ2(Fc)>μ1(Fc) and μ2(Fc)>μ3(Fc): normal wear.

μ3(Fc)>μ1(Fc) and μ3(Fc)>μ2(Fc): severe wear.

μ1(Fc)=μ2(Fc) and μ3(Fc)=0: initial wear.

μ2(Fc)=μ3(Fc) and μ1(Fc)=0: normal wear.

Accordingly, in step S8, after the operation device 50 substitutes the estimated cutting force Fc into the triangular membership function in the fuzzy logic unit, the operation device 50 can respectively obtain three membership degrees μ1(Fc), μ2(Fc) and μ3(Fc). Subsequently, the operation device 50 can determine and output the wear level of the tool 12 in this detection task according to the fuzzy set determination rules.

Figure 4:
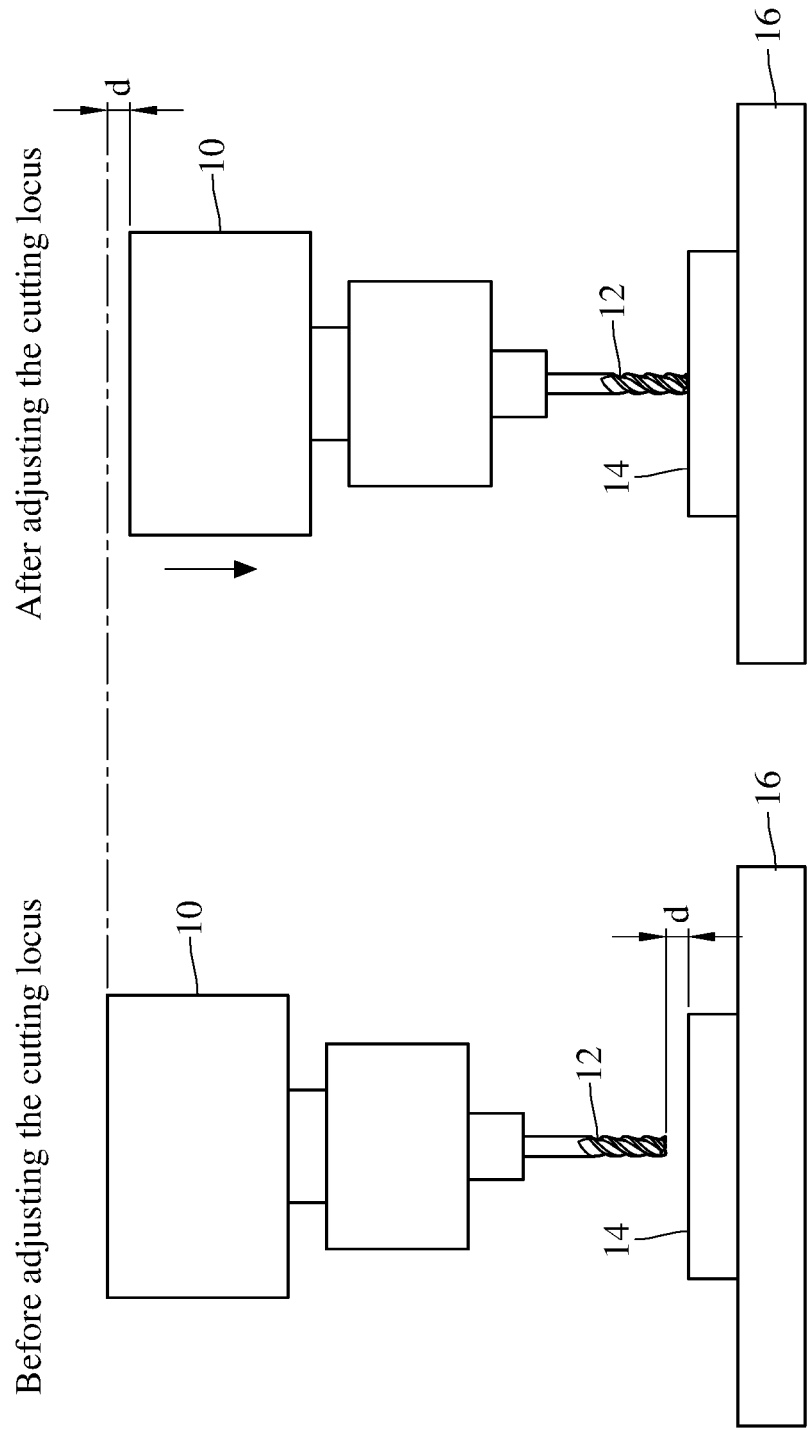
FIG. 4 is a view illustrating the compensation of a tool according to an embodiment of the prevent disclosure.

Refer to step D9 shown in FIG. 2. The control device 30 receives the wear level from outputted by the operation device 50. Further refer to step S91 and FIG. 4, which are associated with the compensation method for tool wear in the present disclosure. If the tool 12 has initial wear or normal wear in this detection task, the control device 30 performs a comparison or lookup in the tool wear database 72 according to the estimated cutting force and the machining parameter sets, to obtain the amount of wear of the tool 12 estimated in this detection task. Then, the control device 30 sets a numerical control instruction for the machine tool 1, e.g. a tool radius compensation instruction G41/G42/G43 provided in the FANUC NC system, and the control device 30 adjusts the cutting locus of the spindle 10 by the numerical control instruction. In a case as shown in FIG. 4, the estimated amount of wear of the tool 12 is d, so the control device 30 moves the spindle of the machine tool 1 downward the workpiece 14 in the Z axis by a distance of d whereby the worn tool 12 contacts the workpiece 14 for machining. In practice, the control device 30 obtains a wear compensation value from a tool-radius wear instruction using a programmable data input instruction, e.g. G10L13PxRx setting, provided by a FANUC NC system, wherein G10 denotes a programmable data input instruction, L13 denotes a tool-radius wear value, Px denotes the ID of the tool 12, and Rx denotes the estimated amount of wear of the tool 12 in this detection task. Accordingly, the control device 30 can automatically be informed of the wear compensation value, and then the control device 30 adjusts the cutting locus of the spindle 10 using this information.

As shown in step S92, if the tool 12 has severe wear in this detection task, the control device 30 issues a warning on the display to notify the user of the need for replacing the tool 12.

Through the compensation method for tool wear in step S91, it is possible to extend the lifespan of the tool 12. In this way, it is possible to make a tool having slight wear achieve the same cutting effect as a tool having no wear. On the other hand, through the real-time warning in step S92, it is possible to prevent the follow-up cutting procedure onto workpieces 14 from being affected by the worn tool 12.

The following table presents the comparison between estimated cutting forces and measured cutting forces of the tools 12 of various wear levels and presents machining parameter sets used in cutting procedures. In view of the following Table, the estimated cutting forces have accuracies of more than 96% in an embodiment of the detection method for tool wear in the present disclosure.

| Wear Level Lookup Table of tool | | | | | | | | |
|---|---|---|---|---|---|---|---|---|
| Cutting depth (mm) | Feeding rate (mm/min) | Cutting speed (m/min) | Total power (W) | Free-load Power (W) | Estimated cutting force (N) | Actual cutting force (N) | Estimated percentage error of cutting force | Status of tool |
| 1 | 344 | 78.539 | 461.165 | 366.938 | 85.74 | 82.439 | 4% | Normal |
| 2 | 344 | 78.539 | 516.061 | 366.938 | 112.48 | 109.129 | 3% | Initial |
| 3 | 344 | 78.539 | 829.789 | 366.938 | 366.16 | 362.996 | 0.8% | Severe |

To sum up, in the detection device, detection method, and compensation method for tool wear provided in the present disclosure, the wear level of a tool is determined by the operation device and the fuzzy logic unit according to current loading rates of the spindle in the tool during the cutting procedure as well as the machining-related information stored in the tool wear database and the machine performance database; and then the wear level is used to decide whether to compensate the cutting locus of the tool or to replace the tool having severe wear. Also, the present disclosure can achieve real-time detection without any additional sensor during the tool is working. Since the detection method can provide more detailed and accurate wear statuses of a tool, the production efficiency of the machine tool may be enhanced and the cost in production equipment may reduce.

What is claimed is:

1. A tool wear detecting method for a machine tool combining a spindle and a tool, comprising:
furnishing the machine tool with a first parameter set including a first cutting depth having a zero cutting depth;
performing a cutting procedure according to the first parameter set by the machine tool, and the tool, and recording a first loading rate of the spindle by a storage device while the cutting procedure is being executed;
furnishing the machine tool with a second parameter set after the cutting procedure is performed according to the first parameter set by the machine tool and the tool, wherein the second parameter set includes a second cutting depth with a non-zero cutting depth;
performing the cutting procedure according to the second parameter set by the machine tool and the tool and recording a second loading rate of the spindle by the storage device while the cutting procedure is being executed;
calculating an estimated cutting force according to the first loading rate, the second loading rate and a machine performance database by an operation device; and
outputting a wear level according to the estimated cutting force and a tool wear database by a fuzzy logic unit of the operation device.

2. The detection method according to claim 1, wherein the first parameter set further comprises a rotational speed, feeding rate and cutting width, and the second parameter set further comprises a rotational speed, feeding rate and cutting width as the same as the first parameter set.

3. The detection method according to claim 1, wherein types of the wear level at least comprise one of initial wear, normal wear and severe wear.

4. The detection method according to claim 1, further comprising before the wear level of the tool is outputted:
obtaining tool samples of various wear levels and measuring an amount of wear of each of the tool samples;
performing the cutting procedure onto respective one of the tool samples according to the second parameter set by the machine tool;
measuring an actual cutting force of each of the tool samples during the cutting procedure by a cutting force dynamometer; and
recording the amount of wear of each of the tool samples and the actual cutting force corresponding to the respective amount of wear into the wear database.

5. The detection method according to claim 4, further comprising after the actual cutting force is recorded into the wear database:
defining a triangular membership function according to the actual cutting force of each of the tools by the operation device; and
generating fuzzy-set membership degrees using the triangular membership function.

6. The detection method according to claim 5, further comprising before the wear level is outputted:
outputting the fuzzy-set membership degrees to a fuzzy set determination rule by the fuzzy logic unit.

7. The detection method according to claim 5, wherein the triangular membership function is:

$$\mu_1(F_c) = \frac{F_2 - F_c}{F_2 - F_1}$$

at $(F_1 \leq F_c \leq F_2)$, $\mu_1(F_c)=1$ at $(F_c \leq F_1)$, and $\mu_1(F_c)=0$ at a relationship among $F_1$, $F_2$ and Fc belonging to neither $(F_1 \leq F_c \leq F_2)$ nor $(F_c \leq F_1)$;

$$\mu_2(F_c) = \frac{F_2 - F_c}{F_2 - F_1}$$

at $(F_1 \leq F_c \leq F_2)$, $$\mu_2(F_c) = \frac{F_3 - F_c}{F_3 - F_2}$$

at $(F_2 \leq F_c \leq F_3)$, and $\mu_2(F_c)=0$ at a relationship among $F_1$, $F_2$, $F_3$ and Fc belonging to neither $(F_1 \leq F_c \leq F_2)$ nor $(F_2 \leq F_c \leq F_3)$; and $$\mu_3(F_c) = \frac{F_c - F_2}{F_3 - F_2}$$

at $(F_2 \leq F_c \leq F_3)$, $\mu_3(F_c)=1$ at $(F_c \geq F_3)$, and $\mu_3(F)=0$ at a relationship among $F_2$ and $F_3$ and Fc belonging to neither $(F_2 \leq F_c \leq F_3)$ nor $(F_c \geq F_3)$;
wherein Fc denotes the estimated cutting force, $F_1$ denotes an initial wear cutting force, $F_2$ denotes a normal wear cutting force, $F_3$ denotes a severe wear cutting force, $\mu_1$ denotes an initial wear membership function, $\mu_2$ denotes a normal wear membership function, and $\mu_3$ denotes a severe wear membership function.

8. The detection method according to claim 7, wherein the fuzzy logic unit further comprises fuzzy set determination rules for determining that the wear level is initial wear, normal wear or severe wear, wherein the fuzzy set determination rules for initial wear comprise:

$(\mu_1(F_c)>\mu_2(F_c))$ and $(\mu_1(F_c)>\mu_3(F_c))$; and
$(\mu 1(Fc)=\mu 2(Fc))$ and $(\mu 3(Fc)=0)$;

the fuzzy set determination rules for normal wear comprise:

$(\mu 2(Fc)>\mu 1(Fc))$ and $(\mu 2(Fc)>\mu 3(Fc))$; and
$(\mu 2(Fc)=\mu 3(Fc))$ and $(\mu 1(Fc)=0)$; and the fuzzy set determination rules for severe wear comprise:

$(\mu 3(Fc)>\mu 1(Fc))$ and $(\mu 3(Fc)>\mu 2(Fc))$.

9. The detection method according to claim 1, further comprising before the estimated cutting force of the tool is calculated:

measuring an actual cutting force of the tool by a cutting force dynamometer during the cutting procedure in the second parameter set;

calculating a cutting power of the tool according to the actual cutting force by the operation device;

calculating a free-load power of the tool according to the first loading rate and the first parameter set by the operation device;

calculating a total power of the tool according to the second loading rate and the second parameter set by the operation device;

calculating a wear coefficient set according to the cutting power, the free-load power and the total power by the operation device; and recording the wear coefficient set into the machine performance database.

10. A compensation method for tool wear, applied to a machine tool comprising a tool connected to a spindle, and comprising:

furnishing the machine tool with a first parameter set including a first cutting depth having a zero cutting depth;

performing a cutting procedure according to the first parameter set by the machine tool, and the tool, and recording a first loading rate of the spindle by a storage device while the cutting procedure is being executed;

setting the machine tool by a second parameter set after the cutting procedure is performed according to the first parameter set by the machine tool and the tool, wherein the second parameter set includes a second cutting depth with a non-zero cutting depth;

performing the cutting procedure according to the second parameter set by the machine tool and the tool, and recording a second loading rate of the spindle by the storage device while the cutting procedure is being executed;

calculating an estimated cutting force according to the first loading rate, the second loading rate and a machine performance database by an operation device;

outputting a wear level according to the estimated cutting force and a tool wear database by a fuzzy logic unit of the operation device; and adjusting cutting locus for the tool according to the wear level by the machine tool.

11. The compensation method according to claim 10, wherein types of the wear level at least comprise initial wear, normal wear and severe wear.

12. The compensation method according to claim 10, wherein adjusting the cutting locus for the tool according to the wear level by the machine tool comprises:

generating a tool radius compensation instruction and setting one or more numerical control instructions of the machine tool according to the wear level by a control device to adjust the spindle of the machine tool, so as to adjust the cutting locus for the tool.

13. The compensation method according to claim 10, wherein adjusting the cutting locus of the tool according to the wear level by the machine tool comprises:

setting a programmable data input instruction according to the wear level and obtaining a wear compensation value from a tool-radius wear instruction to adjust the cutting locus of the spindle in the machine tool by a control device.

14. The compensation method according to claim 10, wherein the control device sets the tool-radius wear instruction according to a programmable data input instruction, a tool-radius wear value, a tool ID and the wear level.

15. A detection device for tool wear, applied to a machine tool comprising a tool connected to a spindle, and comprising:

a control device configured to control a machine tool to perform a cutting procedure respectively according to a parameter set and another parameter set, and output a loading rate and another load rate respectively corresponding to the performing of the cutting procedures, wherein the parameter set is different from the another parameter set in machining parameter;

an operation device configured to calculate a free-load power and a total power according to the loading rate and the another loading rate, calculate a wear coefficient set according to the free-load power, the total power and an actual cutting force, calculate an estimated cutting force according to the wear coefficient set, the free-load power and the total power, and the operation device comprising a fuzzy logic unit for outputting a wear level according to the estimated cutting force and a tool wear database; and a storage device, electrically connected to the control device and the operation device and comprising the wear database, a loading rate database and the machine performance database, the wear database being configured to store another parameter set and an actual cutting force corresponding to the another parameter set; the loading rate database being configured to store the loading rate outputted during the cutting procedure, and the machine performance database configured to store the parameter set, the another parameter set and the wear coefficient set.

16. The detection device according to claim 15, further comprising:

a cutting force dynamometer electrically connected to the spindle and the control device and configured to measure the actual cutting force of the tool connected to the spindle during the cutting procedure, and the control device further configured to receive the actual cutting force and store the actual cutting force into the wear database.

17. The detection device according to claim 15, wherein machining parameters in each of the parameter sets comprise a cutting depth, rotational speed, feeding rate and cutting width.

18. The detection device according to claim 17, wherein the cutting depth in one of the parameter sets is 0, and the cutting depth in the other one of the parameter sets is not 0.

19. The detection device according to claim 15, wherein the fuzzy logic unit comprises a triangular membership function, and the triangular membership function is:

$$\mu_1(F_c) = \frac{F_2 - F_c}{F_2 - F_1}$$

at $(F_1 \leq F_c \leq F_2)$, $\mu_1(F_c)=1$ at $(F_c \leq F_1)$, and $\mu_1(F_c)=0$ at a relationship among $F_1$, $F_2$ and Fc belonging to neither $(F_1 \leq F_c \leq F_2)$ nor $(F_c \leq F_1)$;

$$\mu_2(F_c) = \frac{F_2 - F_c}{F_2 - F_1}$$

at $(F_1 \leq F_c \leq F_2)$, $$\mu_2(F_c) = \frac{F_3 - F_c}{F_3 - F_2}$$

at $(F_2 \leq F_c \leq F_3)$, and $\mu_2(F_c)=0$ at a relationship among $F_1$, $F_2$, $F_3$ and Fc belonging to neither $(F_1 \leq F_c \leq F_2)$ nor $(F_2 \leq F_c \leq F_3)$; and $$\mu_3(F_c) = \frac{F_c - F_2}{F_3 - F_2}$$

at $(F_2 \leq F_c \leq F_3)$, $\mu_3(F_c)=1$ at $(F_c \geq F_3)$, and $\mu_3(F_c)=0$ at a relationship among $F_2$, $F_3$ and Fc belonging to neither $(F_2 \leq F_c \leq F_3)$ nor $(F_c \geq F_3)$, wherein Fc denotes the estimated cutting force, $F_1$ denotes an initial wear cutting force, $F_2$ denotes a normal wear cutting force, $F_3$ denotes a severe wear cutting force, $\mu_1$ denotes an initial wear membership function, $\mu_2$ denotes a normal wear membership function, and $\mu_3$ denotes a severe wear membership function.

20. The detection device according to claim 19, wherein the fuzzy logic unit further comprises fuzzy set determination rules for deciding that the wear level is initial wear, normal wear or severe wear, Wherein the fuzzy set determination rules for initial wear comprise:
($\mu_1(F_c) > \mu_2(F_c)$) and ($\mu_1(F_c) > \mu_3(F_c)$); and
($\mu1(Fc) = \mu2(Fc)$) and ($\mu3(Fc)=0$);

the fuzzy set determination rules for normal wear comprise:
($\mu_2(F_c) > \mu_1(Fc)$) and ($\mu_2(F_c) > \mu_3(F_c)$); and
($\mu_2(F_c) = \mu_3(Fc)$) and ($\mu_1(F_c)=0$); and the fuzzy set determination rules for severe wear comprise:
($\mu3(Fc) > \mu1(Fc)$) and ($\mu3(Fc) > \mu2(Fc)$).

* * * * *